(12) United States Patent
Sefton

(10) Patent No.: US 6,262,117 B1
(45) Date of Patent: *Jul. 17, 2001

(54) METHOD AND COMPOSITION FOR TREATING ACNE

(75) Inventor: John Sefton, Trabuco Canyon, CA (US)

(73) Assignee: Allergan Sales, Inc., Irvine, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,318

(22) Filed: Feb. 18, 1999

(51) Int. Cl.[7] .................. A61K 31/20; A61K 31/075
(52) U.S. Cl. ...................................... 514/558; 514/714
(58) Field of Search .................... 514/198, 284, 514/192, 558, 714

(56) References Cited

U.S. PATENT DOCUMENTS

| | | |
|---|---|---|
| 3,849,396 | 11/1974 | Birkenmeyer . |
| 3,932,653 | 1/1976 | Stoughton . |
| 3,969,516 | 7/1976 | Stoughton . |
| 3,989,816 | 11/1976 | Rajadhyaksha . |
| 3,991,203 | 11/1976 | Rajadhyaksha . |
| 4,018,918 | 4/1977 | Ayer et al. . |
| 4,132,781 | 1/1979 | Stoughton . |
| 4,318,907 * | 3/1982 | Kligman et al. . |
| 4,323,558 | 4/1982 | Nelson . |
| 4,386,104 | 5/1983 | Nazzaro-Porro . |
| 4,387,107 | 6/1983 | Klein et al. . |
| 4,407,794 | 10/1983 | Roques et al. . |
| 4,411,893 | 10/1983 | Johnson et al. . |
| 4,505,896 | 3/1985 | Bernstein . |
| 4,607,101 | 8/1986 | Bernstein . |
| 4,621,075 | 11/1986 | Fawzi et al. . |
| 4,671,956 | 6/1987 | Bouillon et al. . |
| 4,692,329 | 9/1987 | Klein et al. . |
| 4,743,588 | 5/1988 | Mirejovsky et al. . |
| 4,746,675 | 5/1988 | Makino et al. . |
| 4,789,667 | 12/1988 | Makino et al. . |
| 4,803,228 | 2/1989 | Jacquet et al. . |
| 4,882,359 | 11/1989 | Nakagawa et al. . |
| 4,906,617 | 3/1990 | Jacquet et al. . |
| 4,916,118 | 4/1990 | Fidler et al. . |
| 4,942,031 | 7/1990 | Levin . |
| 5,231,087 | 7/1993 | Thornfeldt . |
| 5,260,292 * | 11/1993 | Robinson et al. ............ 514/198 |
| 5,516,950 | 5/1996 | Piccariello et al. . |
| 5,538,732 * | 7/1996 | Smith et al. .................. 424/402 |
| 5,543,417 * | 8/1996 | Waldstreicher ............... 514/284 |
| 5,574,036 | 11/1996 | Bernardon et al. . |
| 5,587,176 | 12/1996 | Warren et al. . |
| 5,612,324 | 3/1997 | Lin et al. . |
| 5,614,178 | 3/1997 | Bloom et al. . |
| 5,618,522 | 4/1997 | Kaleta et al. . |
| 5,643,584 * | 7/1997 | Farng et al. .................. 424/401 |
| 5,665,364 * | 9/1997 | McAtee et al. ............... 424/401 |

FOREIGN PATENT DOCUMENTS

7947764 * 3/1999 (EP) .

OTHER PUBLICATIONS

Leyden et al. Evaluation of the Evaluation of the antimicrobial effects in vivo of Triaz . . . , J. of Dermatological Treatment, 1997, vol. 8/2, pp. S7–S10.*

Tucker et al. Comparison of Topical Clindamycin Phos . . . , BR. J. Dermatol., 1984, vol. 110/4, pp. 487–492.*

Gloor et al. Topical treatment of acne vulgaris . . . , Z. Hautkr. , 1982 vol. 57/12, pp. 867–872, 875, 878.*

Stogmann W., Recommendations for treatment of acne vulgaris, Padiatric und Padologie, 1993, vol.28/3, pp. A33–A35.*

Gollnick et al., Topical therapy in acne, Journal of the European Academy of Dermatology and Venereology, vol. 11/supp. pp. (S8–S12), 1998.*

Mackrides et al., Azelaic acid therapy for acne, American Family Physician, vol. 54/8, pp. 24757–9, 1996.*

Azelex(azelaic acid cream 20%) package insert, Allergan herbert, 1995.*

Gollnick, et al., Topical drug treatment in acne, Dermatology(Basel), vol. 196(1), p. 119–125, 1998.*

Van Hoogdalem, Transdermal absorption of topical anti–acne . . . , J. of the European Academy of Derm. and Vener., vol. 11/suppl.1, p. S13–S19, 1998.*

* cited by examiner

Primary Examiner—William R. A. Jarvis
Assistant Examiner—Vickie Kim
(74) Attorney, Agent, or Firm—Cynthia H. O'Donohue; Robert J. Baran; Martin A. Voet

(57) ABSTRACT

The present invention provides a method for treating acne vulgaris by serially applying a topical composition of azelaic acid and a topical composition of benzoyl peroxide. The present invention also provides topical compositions of a peroxide of benzoyl peroxide, and azelaic acid and its derivatives, such as azelaic acid, sodium salt or methylester which are useful for treating acne vulgaris and may be used to simultaneously apply benzoyl peroxide and azelaic acid.

10 Claims, No Drawings

METHOD AND COMPOSITION FOR TREATING ACNE

FIELD OF THE INVENTION

This invention relates to a method and composition for treating acne vulgaris.

BACKGROUND OF THE ART

Acne vulgaris is an inflammatory disease of the sebaceous glands characterized by an eruption of the skin, often pustular in nature but not suppurative. Acne is a common affliction of the adolescent and affects a small but significant percentage of the adult population. Acne involvement results in unsightly lesions, particularly on the face, and in some cases results in severe scarring.

Various topical agents are utilized in the treatment of acne and these include sulfur, resorcinol, salicylic acid, benzoyl peroxide, retinoids and topical antibiotics. An effective anti-acne agent (or composition) must exhibit the following activities:

(a) a sebostatic activity so as to inhibit hyperseborrhea;

(b) a keratolytic and comedolytic activity so as to avoid hyperkeratosis of the follices and to permit removal of comedos;

(c) a bacteriostatic activity so as to inhibit the activity of Propionibacterium acnes.

Nevertheless, acne vulgaris is seldom cured and only can be contained with difficulty.

The antibiotic clindamycin has been used, topically, to treat acne vulgaris. (See U.S. Pat. No. 3,969,516, to Stoughton.) Various references discuss the use of vehicle formulations to enhance the efficacy of topically-applied clindamycin. (See U.S. Pat. Nos. 3,932,653; 3,989,816; 3,991,203; 4,132,781; 4,671,956; 4,746,675; 4,789,667; 4,803,228 and 4,882,359.) Clindamycin salts, clindamycin derivatives, and various dosage forms of clindamycin have also been discussed as a treatment for acne vulgaris. (See U.S. Pat. Nos. 3,849,396; 4,621,075 and 4,916,118.) Finally, combinations of clindamycin and other compounds active for the treatment of acne vulgaris are disclosed in U.S. Pat. Nos. 4,323,558; 4,505,896; 4,607,101; 4,906,617; 4,942,031 and 4,018,918.

Benzoyl peroxide has been suggested for treating acne vulgaris. (See U.S. Pat. No. 4,387,107.) For many years, benzoyl peroxide has been proven to be a particularly powerful keratolytic and anti-seborrhic agent, as well as being endowed with antibacterial properties. Topical benzoyl peroxide compositions, including a vehicle to enhance the efficacy thereof, are known (See U.S. Pat. No. 4,411,893). Topical compositions of benzoyl peroxide combination with antibiotics are also known. (See U.S. Pat. Nos. 4,407,794; 4,692,329 and 4,387,107)

Peroxides, other than benzoyl peroxide, have been suggested for treatment of acne vulgaris, alone, or in combination with other compounds useful in treating acne vulgaris. (See U.S. Pat. Nos. 4,607,101 and 4,906,617.) These peroxides are suggested as having certain advantages, e.g. stability over benzoyl peroxide. U.S. Pat. No. 4,671,956 identifies the problem of benzoyl peroxide decomposing coingredients in topical formulations to thereby cause itching upon application. It is suggested that this problem may be solved by including a sunscreen in the topical formulation to retard this decomposition effect of benzoyl peroxide.

Azelaic acid has been used topically and systemically to treat acne. See, for example, U.S. Pat. No. 4,386,104 to Nazzo-Pavarro.

In view of the above, it is apparent that there is a great deal of interest in utilizing topical compositions for the treatment of acne vulgaris, such compositions utilizing as an active ingredient clindamycin or benzoyl peroxide or azelaic acid, alone, or in combination with other active ingredients for the treatment of acne vulgaris.

Therefore, one object of the instant invention is to provide a method of treating acne vulgaris with topical compositions including benzoyl peroxide and azelaic acid.

It is another object of the invention to provide a method of treatment of acne vulgaris by topical application of compositions of benzoyl peroxide in a gel form and azelaic acid in a cream form.

It is another object of this invention to provide compositions for the topical treatment of acne vulgaris.

Another object of the invention is to provide topical compositions of benzoyl peroxide and azelaic acid that may be used for treating acne vulgaris.

Other objects and advantages of the instant invention will become apparent from a careful reading of the specification below.

SUMMARY OF THE INVENTION

The present invention provides a method for treating acne vulgaris by topically applying a composition of benzoyl peroxide and azelaic acid, serially, in a therapeutically-effective amount. The azelaic acid or its pharmaceutically acceptable salts or prodrugs (e.g. azelaic acid, sodium salt or lower alkyl ester), may be applied in an amount sufficient to provide from about 0.1 to about 30 percent, and preferably from about 0.5 to about 25 percent, by weight, e.g. about 20 percent azelaic acid. Benzoyl peroxide, which has keratolytic and antiseborrheic properties, may be present in an amount sufficient to provide from about 0.1 to about 30 percent, and preferably from about 2.5 to about 10 percent, by weight, benzoyl peroxide. The benzoyl peroxide may more preferably be used as hydrous benzoyl peroxide and may be suspended preferably in the form of microparticles. The above described topical composition may be in the form of a solution, gel, ointment, cream, a liquid suspension or emulsion or a stick base.

DETAILED DESCRIPTION OF THE INVENTION

The compositions of this invention are administered topically to treat acne vulgaris. That is, the compositions may be applied as a solution, gel, ointment, cream, a liquid suspension or emulsion or a stick base. Thus, it is preferred that such compositions include a pharmaceutically acceptable carrier that enhances the efficacy of such topical administration. Pharmaceutically acceptable carriers include conventional emulsifiers, such as fatty alcohols, glycol ethers and esters of fatty acids; conventional emollients, such as isopropyl and butyl esters of fatty acids, e.g. isopropyl myristate; humectants such as glycerin, propylene glycol, polyethylene glycol; and alcohols and acetone; oils such as mineral oil, petroleum oil, oil extracts from animal or vegetable sources; conventional stabilizers including antioxidants and preservatives. The compositions may also include agents, such as urea, to improve the hydration of the skin. In addition to the foregoing conventional formulations, the topical compositions may include penetration-enhancing agents such as 1-pyrrolidone and N-lower alkyl-2-pyrrolidones, such as N-methyl-2-pyrrolidone; and 1-substituted azacycloalkan-2-ones such as, for example, 1-n-dodecylazacycloheptan-2-one and other compounds disclosed in U.S. Pat. No. 3,989,816. Longer chain sulfoxides, e.g., n-octyl methyl sulfoxide and hexamethylene-lauramide and the other penetration-enhancing agents disclosed in U.S. Pat. No. 4,743,588, may also be included in the formulations utilized in the method of this invention. The amount of these penetration-enhancing agents which may be used in the present invention ranges from about 0.1 to 25 percent and preferably about 1 to 15 percent by weight of the composition.

The amount of the compositions to be administered will obviously be an effective amount for the desired result expected therefrom. This, of course, will be ascertained by the ordinary skill of the practitioner. In accordance with the usual prudent formulating practices, a dosage near the lower end of the useful range of the particular agent may be employed initially and the dosage increased as indicated from the observed response, as in the routine procedure of the physician.

In carrying out the novel method employing the topical route, the active ingredient(s) formulated, for example, as a gel or lotion or suspension, is applied to the affected area of the skin at a rate varying from 0.2 mg per square cm of skin surface per day up to 10 mg per square cm of skin surface per day until the appearance of the affected skin has returned to normal. The gel or lotion or suspension is generally applied for several days.

The topical compositions of this invention may be applied to the face of a patient with acne 1 to 4 times daily with the result that open and closed comedones are markedly reduced within two to four weeks.

The topical composition, including azaleic acid, is preferably a cream formulation. Typically, said cream formulation may comprise:

| FORMULATION A | |
|---|---|
| INGREDIENTS | WEIGHT PERCENT |
| AZELAIC ACID | 20.00 |
| BENZOIC ACID DAB | 0.20 |
| PROPYLENE GLYCOL USP | 12.50 |
| CUTINA CBS(1) | 7.00 |
| PEG-5 GLYCERYL STEARATE(2) | 5.00 |
| CETEARYL OCTANOATE(3) | 3.00 |
| GLYCERIN (85%) DAB | 1.5 |
| PURIFIED WATER DAB(4) | QS |

1. Glyceryl Stearate (and) Cetearyl Alcohol (and) Cetyl Palmitate (and) Cocoglycerides (HENKEL)
2. Arlatone 983S (ICI)
3. PCL Liquid (DRAGOCO)
4. 50.80 percent (w/w)

The topical composition, including benzoyl peroxide, is preferably a gel formulation. Typically, said gel formulation may comprise:

FORMULATION B 4 or 8 percent, by weight, benzyl peroxide in a gel vehicle containing purified water, cetyl alcohol dimethyl isosorbide, fragrance, simethicone, stearyl alcohol and ceteareth-20.

An example of such a product is Brevoxyl® benzyl peroxide available from Stiefel Laboratories, Inc., Coral Gables, Fla.

The invention is further illustrated by the following formulations and examples which are illustrative of a specific mode of practicing the invention and is not intended as limiting the scope of the claims.

EXAMPLE 1

A 20 year old male applies 0.35 gms of the Formulation A and 0.35 gms of Formulation B to his face 4 times daily, each. After 10 days, the number of comedones begin to diminish. By the end of four weeks, the number of comedones declines significantly.

EXAMPLE 2

29 patients were treated, serially, with Formulation A and Formulation B as compared to a control group of 29 patients which was treated with Benzamycin® acne medication, comprising benzyl peroxide 5% and erthyromycin 3%, by weight, available from Dermik Laboratories, Inc., Collegeville, Pa. 19426. 25 patients from each group completed the study. The demographic data for these two groups are reported in Table 1, below.

TABLE 1

| | | Demographic Data | | | | | |
|---|---|---|---|---|---|---|---|
| | | Azelex/BP | | | Benzamycin | | |
| | | Male | Female | Total | Male | Female | Total |
| Age: | n | 11 (37.9%) | 18 (62.1%) | 29 | 5 (17.2%) | 24 (82.8%) | 29 |
| | mean | 20.6[a] | 28.9[a] | 25.8 | 20.7[b] | 30.7[b] | 28.9 |
| | SD | 8.37 | 6.80 | 8.37 | 4.72 | 5.99 | 6.89 |
| | min | 13.3 | 18.8 | 13.3 | 15.0 | 19.4 | 15.0 |
| | max | 39.6 | 39.5 | 39.6 | 25.5 | 44.0 | 44.0 |
| Race:[c] | Black | 5 (45.4%) | 10 (55.6%) | 15 (51.7%) | 0 | 15 (62.5%) | 15 (51.7%) |
| | Caucasian | 6 (54.6%) | 7 (38.9%) | 13 (44.8%) | 5 (100%) | 9 (37.5%) | 14 (48.3%) |
| | Hispanic | 0 | 0 | 0 | 0 | 0 | 0 |
| | Oriental | 0 | 1 (5.6%) | 1 (3.4%) | 0 | 0 | 0 |
| | Other | 0 | 0 | 0 | 0 | 0 | 0 |
| Acne Hx:[d] | <1 year | 0 | 0 | 0 | 0 | 0 | 0 |
| | 1–2 years | 6 (54.6%) | 1 (5.6%) | 7 (24.1%) | 2 (40.0%) | 0 | 2 (6.9%) |
| | 3–5 years | 1 (9.1%) | 3 (16.7%) | 4 (13.8%) | 2 (40.0%) | 2 (8.3%) | 4 (13.8%) |

TABLE 1-continued

Demographic Data

| | Azelex/BP | | | Benzamycin | | |
|---|---|---|---|---|---|---|
| | Male | Female | Total | Male | Female | Total |
| 6–10 years | 1 (9.1%) | 5 (27.8%) | 6 (20.7%) | 1 (20.0%) | 9 (37.5%) | 10 (34.5%) |
| >10 years | 3 (27.3%) | 9 (50.0%) | 12 (41.4%) | (%) | 13 (54.2%) | 13 (44.8%) |

[a]p < 0.05, within Azelex/BP group, for age between, male - female
[b]p < 0.05, within Benzamycin group, for age between, male - female
[c]p < 0.05, within Benzamycin group, for race between, male - female
[d]p < 0.05, within Benzamycin group, for acne history between, male - female The patients were first evaluated for the severity of their acne conditions. This evaluation is reported in Table 2, below.

TABLE 2

Overall Disease Severity

| Visit Number | Treatment Group | n | mean | SD | p-value | Change from Baseline (Week 0) | | | |
|---|---|---|---|---|---|---|---|---|---|
| | | | | | | n | mean | SD | p-value |
| 1 (Week 0) | Azelex/BP | 29 | 3.5 | 1.27 | 0.614 | | | | |
| | Benzamycin | 29 | 3.7 | 1.11 | | | | | |
| 2 (Week 4) | Azelex/BP | 24 | 2.2 | 1.41 | 0.076 | 24 | 1.3 | 1.01 | 0.210 |
| | Benzamycin | 20 | 3.0 | 1.30 | | 20 | 0.9 | 1.25 | |
| 3 (Week 8) | Azelex/BP | 22 | 1.9 | 1.39 | 0.005 | 22 | 1.5 | 1.22 | 0.032 |
| | Benzamycin | 19 | 3.0 | 1.11 | | 19 | 0.7 | 1.25 | |
| 4 (Week 12) | Azelex/BP | 24 | 1.8 | 1.10 | 0.058 | 24 | 1.8 | 1.31 | 0.041 |
| | Benzamycin | 23 | 2.5 | 1.34 | | 23 | 1.0 | 1.26 | |

Note:
Change from baseline = B.L. Visit value minus follow-up Visit value (positive value indicates a decrease from baseline)
Scale (Overall Evaluation of Disease Severity):
0 = None    Normal
1 =         Condition is present, but is less than mild
2 = Mild    Condition is slightly noticeable
3 =         Condition is worse than mild, but less than moderate
4 = Moderate Condition is noticeable
5 =         Condition is worse than moderate, but less than severe
6 = Severe  Condition is very distinctive Over the course of twelve weeks of treatment, the lesion count-pustules and papules are evaluated to determine the effect of the treatment. See Tables 3 and 4.

TABLE 3

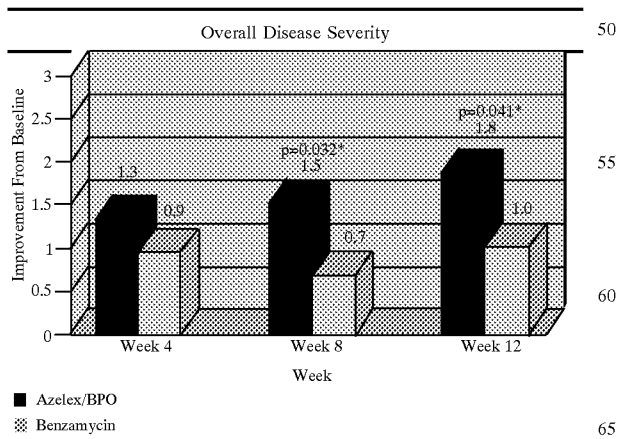

TABLE 4

Lesion Count - Pustules

| Visit Number | Treatment Group | n | mean | SD | p-value | Change from Baseline (Week 0) | | |
|---|---|---|---|---|---|---|---|---|
| | | | | | | n | mean | SD | p-value |
| 1 (Week 0) | Azelex/BP | 29 | 5.4 | 6.59 | 0.566 | | | | |
| | Benzamycin | 29 | 4.1 | 5.70 | | | | | |
| 2 (Week 4) | Azelex/BP | 24 | 1.9 | 3.15 | 0.092 | 24 | 3.6 | 5.95 | 0.329 |
| | Benzamycin | 24 | 2.6 | 2.86 | | 24 | 2.0 | 5.15 | |
| 3 (Week 8) | Azelex/BP | 22 | 1.4 | 3.24 | 0.004 | 22 | 4.6 | 7.44 | 0.313 |
| | Benzamycin | 19 | 2.0 | 1.81 | | 19 | 2.4 | 6.25 | |
| 4 (Week 12) | Azelex/BP | 25 | 1.6 | 3.43 | 0.553 | 25 | 3.8 | 7.70 | 0.141 |
| | Benzamycin | 25 | 2.7 | 7.47 | | 25 | 1.2 | 3.72 | |

As reported in Tables 3 and 4, above, the serial treatment with azaleic acid and benzoyl peroxide is significantly more effective for treating acne than the Benzamycin® control.

Similar evaluations for open comedones, closed comedones and inflammatory lesions show that the method of this invention is more effective than the control.

As to the side effects of treating patients for acne by the method of the invention and the control, the following results were obtained.

| | |
|---|---|
| Scaling. | Azaleic acid (AA)/Benzylperoxide (BPO) is slightly better than the control. |
| Erythema. | AA/BPO is better than the contol. |
| Dryness. | AA/BPO is better than the control. |
| Oilness. | AA/BPO is equal to or slightly worse than the control. |
| Burning. | AA/BPO is better than the control. |
| Itching. | AA/BPO is better than the control. |

While particular embodiments of the invention have been described, it will be understood, of course, that the invention is not limited thereto since many obvious modifications can be made; and it is intended to include within this invention any such modifications as will fall within the scope of the appended claims. For example, it will be appreciated by those skilled in the art that various pharmaceutically acceptable derivatives, salts and prodrugs of azelaic acid, e.g. azelaic acid, sodium or potassium salt, or lower alkyl ester, i.e. $C_1$ to $C_6$ alkyl ester, e.g. methyl azelate, may be used in place of azaleic acid. Also, various forms of peroxides may be used in place of hydrous benzoyl peroxide; i.e., diaryl peroxide, alkyl aryl peroxide, cycloalkyl aryl peroxide, may be substituted for hydrous benzoyl peroxide. For example, lauroyl benzoyl peroxide, cyclohexyl carbanolyl benzoyl peroxide may be used in place of benzoyl peroxide.

Also, the azaleic acid and benzyl peroxide may be combined in a single topical composition, e.g., a cream or gel, for ease of application.

Typically, said single topical composition will comprise the amounts of azelaic acid and benzoyl peroxide sufficient to provide the amounts described above for serial application in a single topical application.

What is claimed is:

1. A topical composition for treating acne vulgaris in human patients consisting essentially of a therapeutically effective amount of benzoyl peroxide and azelaic acid in the absence of retinoids or 5-alpha reductase inhibitors.

2. The composition of claim 1 wherein said benzoyl peroxide and azelaic acid are dispersed in a pharmaceutically acceptable carrier.

3. The composition of claim 2 wherein said composition is a cream or gel.

4. The composition of claim 3 wherein said composition comprises from about 0.1 to 30 percent, by weight, azelaic acid.

5. The composition of claim 4 wherein said composition comprises from about 2.5 to 10 percent, by weight, benzoyl peroxide.

6. The composition of claim 5 wherein said composition comprises about 0.5 to 25 percent, by weight, azelaic acid.

7. The composition of claim 6 wherein said composition comprises about 20 percent, by weight, azelaic acid.

8. A method of treating acne vulgaris in human patients which comprises topically administering to said patients a composition according to claim 1.

9. A method of treating acne vulgaris in human patients which comprises topically administering to said patients a composition according to claim 4.

10. A method of treating acne vulgaris in human patients which comprises topically administering to said patients a composition according to claim 7.

* * * * *

UNITED STATES PATENT AND TRADEMARK OFFICE
CERTIFICATE OF CORRECTION

PATENT NO.   : 6,262,117 B1
DATED        : July 17, 2001
INVENTOR(S)  : Sefton

Page 1 of 1

It is certified that error appears in the above-identified patent and that said Letters Patent is hereby corrected as shown below:

<u>Columns 5 and 6,</u>
Delete "$^a$p" and insert in place thereof -- a = p --.
Delete "$^b$p" and insert in place thereof -- b = p --.
Delete "$^c$p" and insert in place thereof -- c = p --.
Delete "$^d$p" and insert in place thereof -- d = p --.

Signed and Sealed this

Twenty-ninth Day of January, 2002

Attest:

JAMES E. ROGAN
*Attesting Officer*  *Director of the United States Patent and Trademark Office*